United States Patent
Nozato (10) Patent No.: US 10,492,681 B2
(45) Date of Patent: Dec. 3, 2019

(54) SYSTEM AND METHOD OF BLINK DETECTION FOR AN ADAPTIVE OPTICS SYSTEM

(71) Applicant: CANON KABUSHIKI KAISHA, Tokyo (JP)

(72) Inventor: Koji Nozato, Rochester, NY (US)

(73) Assignee: Canon Kabushiki Kaisha, Tokyo (JP)

( * ) Notice: Subject to any disclaimer, the term of this patent is extended or adjusted under 35 U.S.C. 154(b) by 34 days.

(21) Appl. No.: 14/558,574

(22) Filed: Dec. 2, 2014

(65) Prior Publication Data
US 2015/0150450 A1     Jun. 4, 2015

Related U.S. Application Data

(60) Provisional application No. 61/911,326, filed on Dec. 3, 2013.

(51) Int. Cl.
*A61B 3/113*     (2006.01)
*A61B 3/10*      (2006.01)
(Continued)

(52) U.S. Cl.
CPC ............ *A61B 3/113* (2013.01); *A61B 3/1015* (2013.01); *A61B 3/1025* (2013.01); *A61B 3/11* (2013.01); *A61B 3/14* (2013.01)

(58) Field of Classification Search
CPC ......... A61B 3/1015; A61B 3/11; A61B 3/113; A61B 3/14
(Continued)

(56) References Cited

U.S. PATENT DOCUMENTS 6,217,172 B1 *  4/2001 Shibutani ............... A61B 3/103
                                                    351/204
7,559,651 B2    7/2009 Shimizu et al.
(Continued)

FOREIGN PATENT DOCUMENTS

WO   2010/052497 A1   5/2010
WO   2013/125545 A1   8/2013
WO   2013/125547 A1   8/2013

OTHER PUBLICATIONS

Kenichi Saito, Koji Nozato, Kei Suzuki, Austin Roorda, Alfredo Dubra, Hongxin Song, Jennifer J. Hunter, David R. Williams, Ethan A. Rossi, Rods and Cones Imaged With a Commercial Adaptive Optics Scanning Light Ophthalmoscope (AOSLO) Prototype, Investigative Ophthalmology & Visual Science, May 2, 2014 55: E-Abstract 1594-D0009, The Association for Research in Vision and Ophthalmology, Inc., Rockville, MD, 2014.
(Continued)

*Primary Examiner* — Zachary W Wilkes
(74) *Attorney, Agent, or Firm* — Canon U.S.A., Inc. I.P. Division (57) ABSTRACT

An optical imaging system, method, and medium for imaging a subject. Measure an aberration state of light from the subject is measured. Determine a condition of the subject based on the aberration state of the light, and if the subject is in a first condition or a second condition. An aberration correction device that adjusts a state of the light. In a first case if the subject is in the first condition than the light is adjusted based on the aberration state of the light used to determine that the subject is in the first condition. In a second case if the subject is in the second condition than the light is adjusted based on based on a most recent aberration state of the light that was used to determine that the subject was in the first condition prior to detecting that the subject is in the second condition.

26 Claims, 7 Drawing Sheets

(51) Int. Cl.
*A61B 3/14* (2006.01)
*A61B 3/11* (2006.01)

(58) Field of Classification Search
USPC .................................... 351/206, 210, 209
See application file for complete search history.

(56) References Cited

U.S. PATENT DOCUMENTS

| | | | |
|---|---|---|---|
| 7,677,728 B2* | 3/2010 | Hirohara | A61B 3/101 351/206 |
| 7,791,734 B2 | 9/2010 | Olivier et al. | |
| 7,988,293 B2* | 8/2011 | Raymond | A61B 3/1015 351/221 |
| 8,113,658 B2 | 2/2012 | Warden et al. | |
| 8,262,222 B2 | 9/2012 | Levecq et al. | |
| 8,444,268 B2 | 5/2013 | Hammer et al. | |
| 8,777,410 B2* | 7/2014 | Hanebuchi | A61B 3/1025 351/206 |
| 2008/0225228 A1* | 9/2008 | Saito | A61B 3/1015 351/206 |
| 2011/0115042 A1 | 5/2011 | Nozato | |
| 2011/0149239 A1* | 6/2011 | Neal | A61B 3/0025 351/205 |
| 2012/0176581 A1 | 7/2012 | Bradley et al. | |
| 2013/0100405 A1* | 4/2013 | Porter | A61B 3/1015 351/206 |
| 2013/0321766 A1 | 12/2013 | Morohashi | |
| 2014/0146286 A1 | 5/2014 | Suzuki | |

OTHER PUBLICATIONS

Kenichi Saito, Koji Nozato, Kei Suzuki, Austin Roorda, Alfredo Dubra, Hongxin Song, Jennifer J. Hunter, David R. Williams, Ethan A. Rossi, Rods and Cones Imaged With a Commercial Adaptive Optics Scanning Light Ophthalmoscope (AOSLO) Prototype, ARVO Annual Meeting 2014, Orlando, FL, Poster #1594-D0009, May 5, 2014.

Betul Sahin, Barbara Lamory, Xavier Levecq, Fabrice Harms, Chris Dainty, Adaptive Optics with Pupil Tracking for High Resolution Retinal Imaging, Biomedical Optics Express, Feb. 1, 2012, 3(2);225-239, Optical Society of America, Washington DC.

Daniel X. Hammer, R. Daniel Ferguson, Chad E. Bigelow, Nicusor V. Iftimia, Teoman E. Ustun, Adaptive Optics Scanning Laser Ophthalmoscope for Stabilized Retinal Imaging, Optics Express, Apr. 17, 2006, 14(8):3354-3367, Optical Society of America, Washington DC.

Betul Sahin, Correction of the Aberrations of the Eye using Adaptive Optics with Pupil Tracking, Aug. 2011, pp. 1-173, Applied Optics Group, School of Physics, National University of Ireland, Galway, IR.

R. Daniel Ferguson, Daniel X. Hammer, Chad E. Bigelow, Nicusor V. Iftimia, Teoman E. Ustun, Stephen A. Burns, Ann E. Elsnerm, David R. Williams, Tracking Adaptive Optics Scanning Laser Ophthalmoscope, pp. 1-9, Mar. 7, 2006.

* cited by examiner

SYSTEM AND METHOD OF BLINK DETECTION FOR AN ADAPTIVE OPTICS SYSTEM

CROSS-REFERENCE TO RELATED APPLICATION

This application claims the benefit of U.S. Provisional Application No. 61/911,326, filed Dec. 3, 2013 which is hereby incorporated by reference herein in its entirety.

BACKGROUND

Field of Art

The present disclosure relates to a system and method for detecting blinks in an ophthalmoscope.

Description of the Related Art

In recent years, scanning light ophthalmoscopes (SLOs) that irradiate the fundus with laser light in two dimensions and receive reflected light therefrom and imaging apparatuses that utilize the interference of low coherence light have been developed as ophthalmic image pickup apparatuses. Thus, SLOs have become important tools for the study of the human retina in both normal and diseased eyes.

The resolution of such ophthalmic image pickup apparatuses has been improved by, for example, achieving high NA of irradiation laser light. However, when an image of the fundus is to be acquired, the image must be acquired through optical tissues including the cornea and the crystalline lens. As the resolution increases, the aberrations of the cornea and the crystalline lens have come to significantly affect the quality of acquired images.

One solution to this issue is an adaptive optics SLO (AO-SLO) in which the adaptive optics (AO) includes a correction optical system that measures the aberration of the eye and corrects the aberration. The AO-SLO or an adaptive optics optical coherence tomograph (AO-OCT) can measure the wavefront of the eye using a Shack-Hartmann wavefront sensor system. A deformable mirror or a spatial-phase modulator can then be driven to correct the measured wavefront, and an image of the fundus is acquired can then be acquired. This technique allows for the AO-SLO or the AO-OCT to obtain high resolution images of fundus despite the distortion introduced by intervening material such as the cornea and the lens of the eye.

SUMMARY

In one embodiment, an optical imaging system for imaging a subject. The system includes one or more optical components for receiving light and transmitting the received light to a subject to be imaged. The system includes an aberration detection device that measures an aberration state of light from the subject. The system includes a controller that determines a condition of the subject based on the aberration state of the light detected by the aberration detection device, and determines if the subject is in a first condition or a second condition. The system includes an aberration correction device that adjusts a state of the light. Wherein in a first case if the subject is in the first condition then the aberration correction device adjusts the light based on the aberration state of the light detected by the aberration detection device that was used to determine that the subject is in the first condition. Wherein in a second case if the subject is in the second condition then the aberration correction device adjusts the aberration state of the light based on a most recent aberration state of the light detected by the aberration detection device that was used to determine that the subject was in the first condition prior to detecting that the subject is in the second condition.

In another embodiment, the subject is an eye. The second condition is that the eye is in the process of blinking. The first condition is that the eye is not in the process of blinking.

In another embodiment, determining that the eye is in the process of blinking is detected by: calculating a change in a size of a pupil of the eye based upon the measured aberration state of the light detected by the aberration detection device; and calculating a change in a position of the pupil of the eye based upon the measured aberration state of the light detected by the aberration detection device.

In another embodiment, if the change in the size of the pupil indicates that pupil size has decreased relative to a previous size of the pupil when the eye was last determined to be in the first condition; and if the change in the position is such that a vertical displacement of the pupil is larger than a horizontal displacement of the pupil, relative to a previous position of the pupil when the eye was last determined to be in the first condition, then the eye is determined to be in the process of blinking, otherwise the eye is determined to not be in the process of blinking.

In another embodiment, the aberration correction device adjusts one or both of: aberration state of light from the subject, and aberration state of light to the subject.

In another embodiment, the aberration correction device is a wavefront correction device.

In another embodiment, the wavefront correction device is selected from one or more of a tip-tilt mirror, a deformable mirror, a fluidic lens, and a spatial light phase modulator.

In another embodiment, the aberration detection device is a wavefront sensor.

In another embodiment, the wavefront sensor is a Shack-Hartmann sensor.

In another embodiment, if the controller detects eye lid or eye lash movement then the controller determines that the subject is in the second condition.

In another embodiment, in the second case the aberration correction device maintains the state of the light while the subject is in the condition until the subject returns to the second condition.

In another embodiment, when the subject switches from the second condition to the first condition a process control loop that includes the aberration detection device and aberration correction device is reset.

In another embodiment, the optical imaging system further comprises a light source which produces light which is received by the one or more optical components.

In another embodiment, the optical imaging system further comprises one or more scanners for scanning the light across the subject and a detector for detecting light from the subject.

In another embodiment, is an optical imaging method for imaging a subject. The optical imaging method includes measuring an aberration state of light from the subject. The optical imaging method includes detecting a condition of the subject based on the aberration state of the light. The optical imaging method includes determining if the subject is in a first condition or a second condition. The optical imaging method includes adjusting a state of the light, wherein: in a first case if the subject is in the first condition then the state of the light is adjusted based on the aberration state of the light that was used to determine that the subject is in the first condition; and in a second case if the subject is in the second condition then the state of the light is adjusted based on a most recent aberration state that was used to determine that the subject was in the first condition prior to determining that the subject is in the second condition.

Another embodiment, is a computer readable medium encoded with instructions for the optical imaging method.

BRIEF DESCRIPTION OF THE DRAWINGS

The accompanying drawings, which are incorporated in and constitute a part of the specification, illustrate exemplary embodiments.

DESCRIPTION OF THE EMBODIMENTS

Embodiments will be described below with reference to the attached drawings. Like numbers refer to like elements throughout. Exemplary embodiments will be described in detail with reference to the drawings below. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an image photographing apparatus as disclosed in the following can be applied to an object to be inspected such as an eye to be inspected, skin, and internal organs.

Ophthalmoscope

A first embodiment is described with reference to a fundus image photographing apparatus such as the photographing apparatus illustrated in FIG. 1.

Embodiments are directed towards systems, methods, and software which are used in connection with an imaging system such as an ophthalmoscope. FIG. 1 is an illustration of an exemplary ophthalmoscope. An ophthalmoscope is a system or apparatus for obtaining information about an interior portion of the eye 111 (e.g., the fundus).

An exemplary embodiment may be a scanning ophthalmoscope. A scanning ophthalmoscope scans a spot across the eye. The spot may be a spot of light from a light source that is scanned across the eye.

Figure 1:
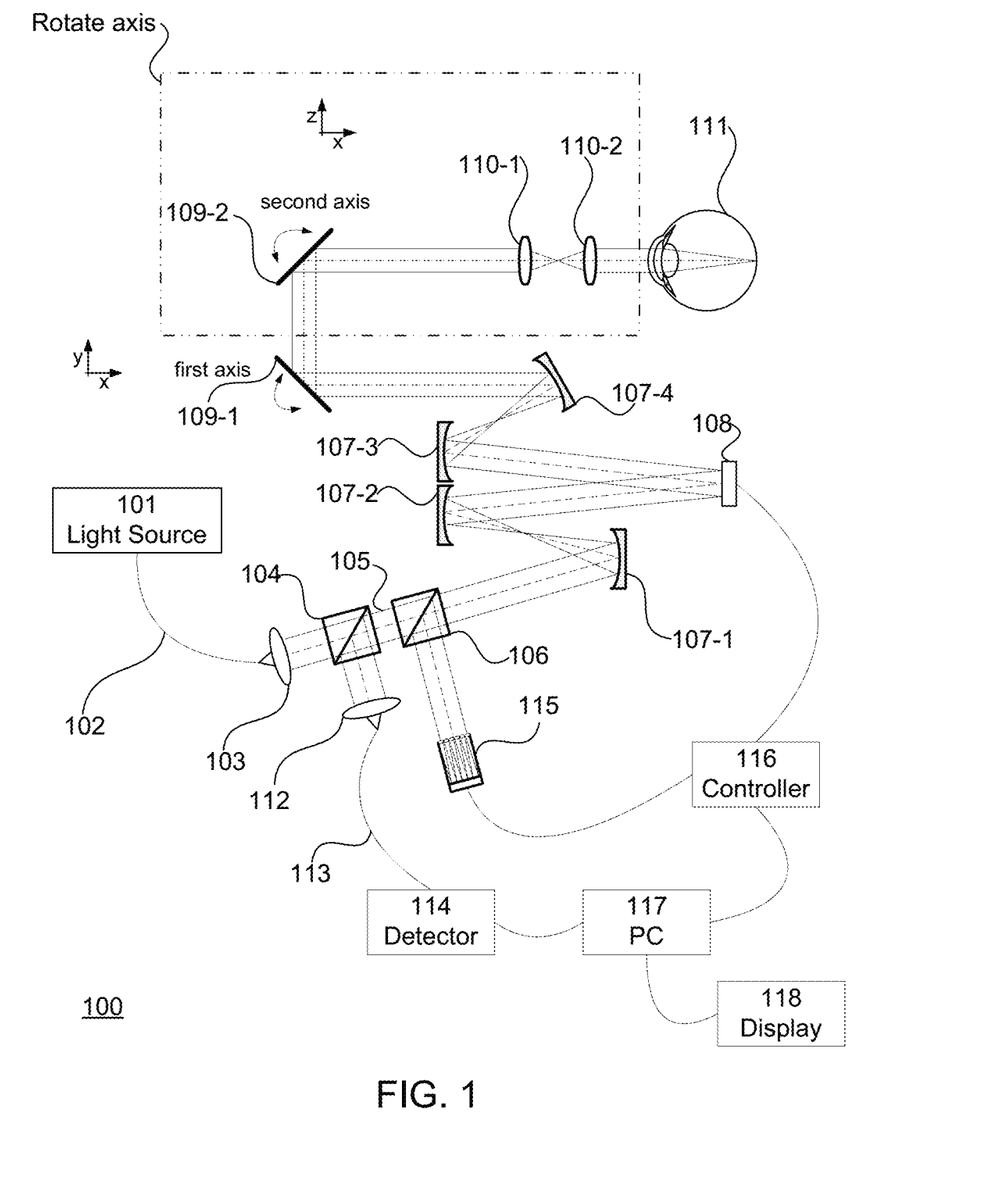
FIG. 1 is an illustration of an exemplary embodiment.

In an exemplary embodiment illustrated in FIG. 1, a spot of light is produced by a light source 101. The light source 101 may be incorporated into the ophthalmoscope 100; alternatively, the ophthalmoscope may include an input for receiving a light source 101. The input for the light source 101 may be a fiber optic input or a free space input. The light source 101 may be a laser, a broadband light source, or multiple light sources. In an exemplary embodiment, the light source 101 is a super luminescent diode (SLD) light source having a wavelength of 840 nm. The wavelength of the light source 101 is not particularly limited, but the wavelength of the light source 101 for fundus image photographing is suitably set in a range of approximately 800 nm to 1,500 nm in order to reduce glare for a person to be inspected and maintain imaging resolution.

In an exemplary embodiment, light emitted from the light source 101 passes through a single-mode optical fiber 102, and is radiated as collimated light (measuring light 105) by a collimator 103.

In an exemplary embodiment, the polarization of the irradiated light may be adjusted by a polarization adjusting member 119 (not shown) provided in a path of the single-mode optical fiber 102. In an alternative configuration, the light source 102 is polarized and single-mode optical fiber 102 is polarization maintain fiber. In another configuration, the polarization adjusting member may be placed after the collimator 103. Alternatively, the polarization adjusting member may be replaced with a polarizer.

The measuring light 105 radiated from the collimator 103 passes through a light division portion 104 including a beam splitter. An exemplary embodiment includes an AO system.

The AO system includes a light division portion 106, a wavefront sensor 115, wavefront correction device 108, and reflective mirrors 107-1 to 107-4 for guiding the measuring light 105 to those components. The reflective mirrors 107-1 to 107-4 are provided to guide the measuring light 105 to and from the pupil of an eye 111, the wavefront sensor 115, and the wavefront correction device 108. The wavefront sensor 115 and the wavefront correction device 108 may be in an optically conjugate relationship. A beam splitter may be used as the light division portion 106. The wavefront sensor 115 may be a Shack-Hartmann sensor or any other sensor that provides information about the wavefront.

The measuring light 105 passing through the light division portion 106 is reflected on the reflective mirrors 107-1 and 107-2 to enter the wavefront correction device 108. The measuring light 105 reflected on the wavefront correction device 108 and is further reflected on the reflective mirrors 107-3 and 107-4.

In one embodiment, the wavefront correction device 108 is a deformable mirror or a tip/tilt mirror. In an alternative embodiment, one or two spatial phase modulators including a liquid crystal element is used as the wavefront correction device 108 which is not illustrated. The liquid crystal element may modulate a phase of only a specific polarized component. In which case, two liquid crystal elements may be employed to modulate substantially orthogonal polarized components of the measuring light 105. The wavefront correction device 108 is an example of aberration correction device. Other aberration correction devices which use other techniques for correcting the aberration, such as devices which use geometrical optics or fluidic lenses or an adjustable aperture, may be used in other embodiments. The wavefront correction device may use multiple techniques in series or may switch between different techniques depending on the nature of the aberration.

The measuring light 105 reflected off mirror 107-4 is two-dimensionally scanned by a scanning optical system 109 which may be part of a scanning unit. In an exemplary embodiment, the scanning optical system 109 includes a first scanner 109-1 and a second scanner 109-2. The first scanner 109-1 may be part of a first scanning unit. The second scanner 109-2 may be part of a second scanning unit. The first scanner 109-1 rotates around the first axis, while the second scanner 109-2 rotates around a second axis. The first axis is substantially orthogonal to the second axis.

FIG. 1 illustrates the first scanner 109-1 rotating in the x-y plane, while the second scanner 109-2 is rotating in the z-x plane. In the context of the present application, rotating the measuring light 105 in a first plane around the first axis is equivalent to rotating the measuring light 105 in the first plane and is equivalent to scanning the spot of light in the main scanning direction or the lateral direction of the object being imaged. In the context of the present application, rotating the measuring light 105 in a second plane around the second axis is equivalent to rotating the measuring light 105 in the second plane and is equivalent to scanning the spot of light in the sub-scanning direction or the longitudinal direction of the object being imaged. The sub-scanning direction is substantially orthogonal to the main scanning direction.

A scanning period of the first scanner 109-1 is less than the scanning period of the second scanner 109-2. The order of the first scanner 109-1 and the second scanner 109-2 may be exchanged without impacting the operation of an exemplary embodiment. The first scanner 109-1 may operate in a resonant scanning mode.

In an exemplary embodiment, the scanning optical system 109 may be a single scanning mirror that is rotated around the first axis by the first scanner 109-1 and around the second axis by the second scanner 109-2 that is substantially orthogonal to the first axis. An exemplary embodiment may also use non-mechanical beam steering techniques may also be used.

In an exemplary embodiment, the first scanner 109-1 and the second scanner 109-2 are galvano-scanners. In another exemplary embodiment, one of the first scanner 109-1 and the second scanner 109-2 is a resonant scanner. The resonant scanner may be used for the main scanning direction. The resonant scanner may be tuned to oscillate at a specific frequency.

The measuring light 105 scanned by the scanning optical system 109 is radiated to the eye 111 through eyepieces 110-1 and 110-2. The measuring light radiated to the eye 111 is reflected, scattered, or absorbed on the fundus. When the eyepieces 110-1 and 110-2 are adjusted in position, suitable irradiation may be performed in accordance with the diopter of the eye 111. Lenses may be used for the eyepiece portion in this embodiment, but other optical components such as spherical mirrors may also be used.

Reflected light which is produced by reflection or scattering on a retina of the eye 111 then travels in the reverse direction along the same path as in the case of incident light. A part of the reflected light is reflected by the light division portion 106 to the wavefront sensor 115 to be used for measuring a light beam wavefront.

In an exemplary embodiment, a Shack-Hartmann sensor is used as the wavefront sensor 115. However, an exemplary embodiment is not limited to a Shack-Hartmann sensor. Another wavefront measurement unit, for example, a curvature sensor, an interferometer, or a method of obtaining the wavefront by reverse calculation from the formed spot images, may be employed. The wavefront sensor 115 is an example of an aberration sensor. An aberration sensor may be a combination of hardware and software that is used to determine the condition of the imaging system and/or the condition of the subject which has an impact on the imaging performance of the ophthalmoscope 100. The aberration sensor may output a signal that represents the aberration state of the light from the subject.

In FIG. 1, when the reflected light passes through the light division portion 106, a part thereof is reflected on the light division portion 104 and is guided to a light intensity sensor 114 through a collimator 112 and an optical fiber 113. The light intensity sensor 114 converts the light into an electrical signal. The electrical signal is processed by a PC 117 into an image of the object, and the image is displayed on a display 118.

The controller 116 and the PC 117 may include one or more computer-readable or computer-writable media, for example a computer-readable storage medium. A computer-readable storage medium, in contrast to a mere transitory, propagating signal, includes a tangible article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). The media can store computer-readable data or computer-executable instructions. The media components of controller 116 and the PC 117 may communicate via a bus. One or more modules for implementing a method or controlling the ophthalmoscope 100 includes logic, computer-readable data, or computer-executable instructions, and may be implemented in software (e.g., Assembly, C, C++, C#, Java, BASIC, Perl, Visual Basic), hardware (e.g., customized circuitry), or a combination of software and hardware. In some embodiments, the devices in the system include additional or fewer modules, the modules are combined into fewer modules, or the modules are divided into more modules. Instructions for executing a method described herein may be stored on a computer-readable storage medium. Instructions for executing a method described herein may be stored on a non-transitory computer-readable storage medium.

The wavefront sensor 115 is connected to an AO control unit 116. The received wavefront is transferred to the AO control unit 116. The wavefront correction device 108 is also connected to the AO control unit 116 and performs modulation as instructed by the AO control unit 116. The AO control unit 116 calculates a modulation amount (correction amount) for correction to obtain wavefront having no aberration based on the wavefront obtained by a measuring result of the wavefront sensor 115, and instructs the wavefront correction device 108 to perform the modulation according to the modulation amount. The wavefront measurement and the instruction to the wavefront correction device are repeated and feedback control is performed so as to obtain a suitable wavefront.

In an exemplary embodiment the light division portion 104 is a fused fiber coupler. In an alternative exemplary embodiment, the light division portions 104 and 106 include partially reflective mirrors.

The detector 114 may detect reflections or fluorescence associated with the scanning spot. The detection system may make use confocal microscopy techniques in which an aperture associated with the scanning spot is used to increase the resolution and/or contrast of the detection system. The system may also include a reference arm and the detection system may be used to detect an interference signal.

AO Feedback System

Figure 2:
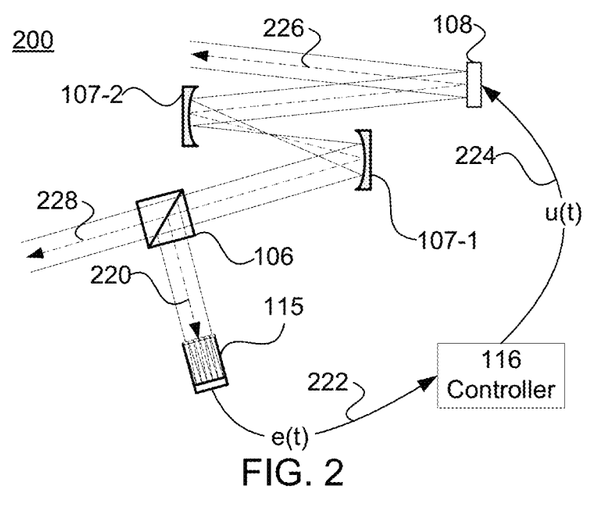
FIG. 2 is an illustration of a feedback system.

An AO system such as the one used in the ophthalmoscope 100 is illustrated in FIG. 2. FIG. 2 illustrates the optical components of a feedback loop system 200. The optical components of the feedback loop system 200 comprises at least: the wavefront sensor 115, the wavefront correction device 108 and the controller 116. The feedback loop system may also include a light division portion 106 and mirrors 107-1 to 107-2. Light from the light source 101 passes through the light division portion 106 is reflected off mirrors 107-1 to 107-2 it is then corrected by the wavefront correction device 108 before it is sent off to the eye 111. Light is then gathered from the eye 111 and corrected by the wavefront correction device before being passed onto the wavefront sensor 115 via mirrors 107-1 to 107-2 and light division portion 106. The light division portion 106 will pass along a portion of the light to wavefront sensor 106 while the rest of the light is passed along to the detector 114. The process is repeated continuously.

The wavefront sensor 115 measures a portion 220 of the beam of light from the eye 111 to determine a residual wavefront error signal 222 e(t), which is sent to the controller 116. The controller 116 sends a control signal 224 to the wavefront correction device 108. The control signal 224 u(t) may be based on one or more of the current and past residual wavefront error signals 222 and past control signals 224. The wavefront correction device 108 will then adjust the wavefront of light as it sent to the eye 111 as beam 226. The wavefront correction device 108 also adjusts the wavefront of light from the eye 111 as beam 228 a portion of which split off from beam 228 to become new portion 220 which once again used to determine a new residual wavefront error signal 222. Thus, closing the feedback loop 200. Beam 228 is then sent onto detector 114.

The residual wavefront error signal 222 and control signal 224 may be arrays of signal data. Thus, the feedback loop system 200 involves measuring aberration and aberration correction which is processed one after another continuously by the controller 116.

Corresponding to movement of the eye 111 and constriction of the pupil of the eye 111, the wavefront sensor 115 measures the pupil size and position and the control area of correction device 108 is changed according to the pupil size and position measured by the wavefront sensor 115. The aberration measured by the wavefront sensor 115 is different for different pupil sizes. This can affect the AO feedback system 200 such that the feedback control can take several cycles to return to well compensated AO condition.

The eye 111 may blink one or more times during AO-SLO imaging. AO-SLO imaging can take a few seconds to take sufficient images for each imaging position. During blinking, the detected pupil size as measured by the wavefront sensor 115 can change due to measured aberrations that occur while the eye 111 is blinking. This can impact AO feedback systems. Especially systems in which the control area is changed in response of the detected pupil size. This can cause the AO feedback loop to become unstable during blinking.

The applicants have found that the aberration as measured by the wavefront sensor 115 after blinking is substantially similar and will be almost same as the aberration before blinking. So it is important to detect blinking, to ignore the pupil size change and to restart AO control when the pupil size returns to the original condition. The human pupil also constricts during imaging and this needs to be distinguished from blinking.

AO Feedback Method

Figure 3:
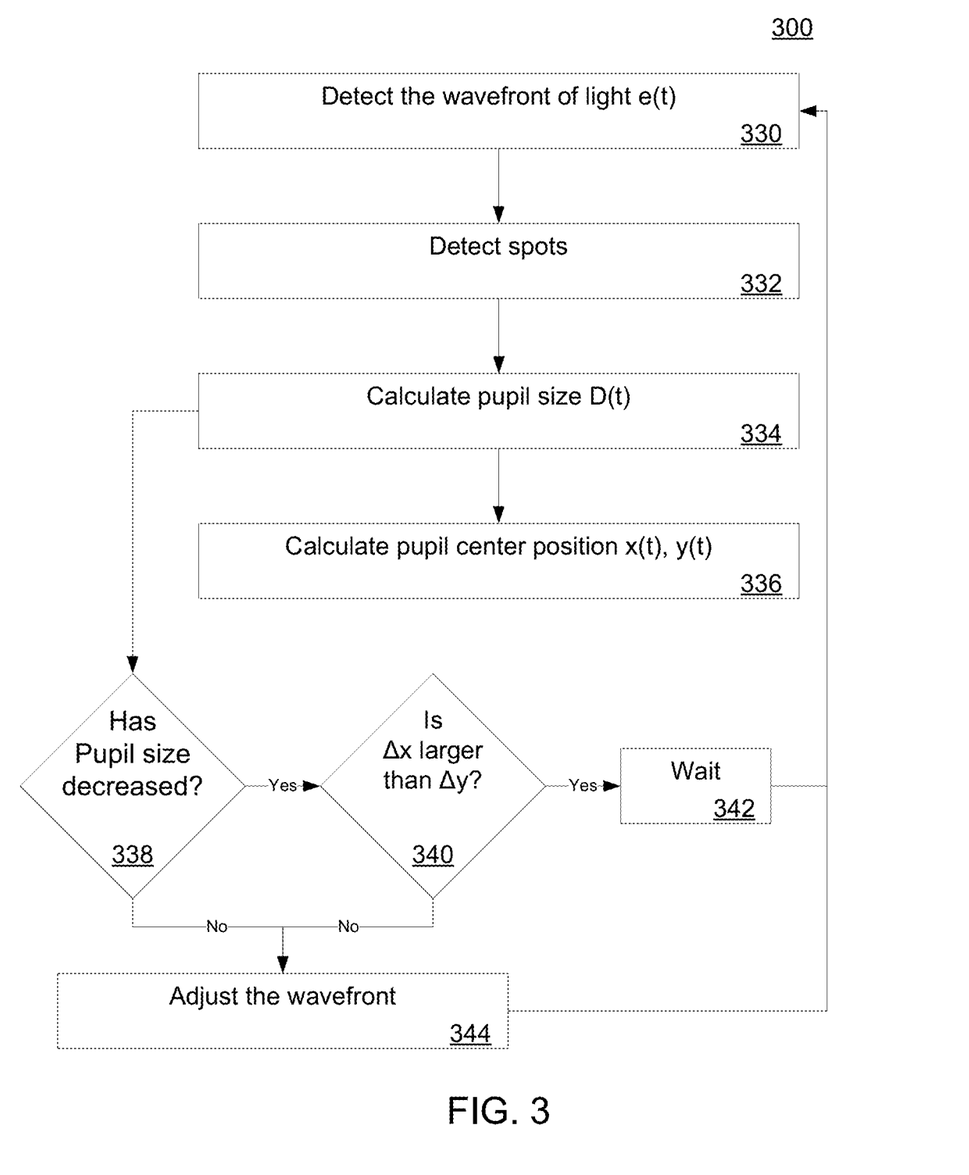
FIG. 3 is and illustration of a feedback method used in an exemplary embodiment.

An embodiment may include a feedback control method 300 illustrated in FIG. 3. The feedback control method 300 may be implemented in hardware, software or a combination of hardware and software.

A first step in the method may include a first step 330 of detecting the wavefront of light from the eye 111. The wavefront of the light from the eye is detected with a wavefront sensor 115 and may be a Shack-Hartmann sensor. The signal 222 from the wavefront sensor 115 may take the form of a Hartmann image.

The controller 116 may then detect spots in the Hartmann image in a second step 332. Controller 116 may use a peak detection method to identify bright spots, wherein intensity peaks with a sufficient brightness above a threshold are recognized as spots. The second step 332 may also include alternative methods of analyzing the wavefront detected by the wavefront sensor 115.

In a third step 334, the controller calculates the pupil size (D(t)) at a time index (t) based on the information 222 provided by the wavefront sensor 115 which may be based on the spots in the Hartmann image detected in the second step 332 or based directly on the information 222 provided by the wavefront sensor 115. Wherein the variable D(t) is an estimated diameter of the pupil size at time index t based on the detected wavefront sensor data.

In a fourth step 336, the pupil center position (x(t), y(t)) at a time index (t) is calculated by the controller 116 from the spots in the Hartmann image or based directly on the information 222 provided by the wavefront sensor 115. Wherein the variable x(t) is an estimated horizontal position of the pupil center based on the detected wavefront sensor data at time index (t). Wherein the variable y(t) is an estimated vertical position of the pupil center based on the detected wavefront sensor data at time index (t). The controller 116 may include a subroutine for calculating the size of the pupil D(t). In a first sub-step the controller may calculate an area in the Hartmann image filled with spots. The controller 116 in a second sub-step may identify the edges of the area filled with spots. The controller 116 in a third sub-step may then calculate diameter and position of the largest circle inside the detected area.

In a fifth step 338, the controller 116 calculates if the diameter has decreased. This step may be performed after the pupil size D(t) has been calculated and before or after the pupil center position is calculated in the fourth step 336. This may be done by checking if D(t)<D(t−1). If the answer is yes then the next step is step 340. If the answer is no then the next step is step 344. In an alternative embodiment, this is done by checking D(t)<D(t−n), wherein n is first initialized as 1. If the answer is yes then the next step is step 340 and n=n+1 after step 342. If the answer is no then the next step is step 344 and n is equal to 1.

In a sixth step 340, the controller 116 determines if the displacement of the pupil in vertical direction is larger than that in the horizontal direction. This may be done by first calculating the displacements Δx(t)=x(t)−x(t−1) and Δy(t)=y(t)−y(t−1). Then the displacements are compared by checking Δy(t)>Δx(t). If the answer is yes then the next step is step 342. If the answer is no then the controller has determined that the eye 111 is blinking and the next step is the eighth step 344.

If in the sixth step 340 the controller 116 has determined that the eye 111 is blinking and the controller 116 moves on to the seventh step and waits until the pupil size D(t) returns to the size before the blinking was detected. This may be done by either waiting or by constantly checking the size of the pupil of the eye 111. During the seventh step 342 the controller 116 keeps the control signal 224 as the same value as previously used before the blink was detected before step 342. After the controller has done waiting and the pupil returns to the previous size, then and the control loop moves back to step 330 to re-measure the residual wavefront error signal 222 e(t) at the start of the method 300 in step 330. During this step, the control signal 224 sent to the wavefront correction device 108 is held constant either by remembering the previous value of the control signal 224 before the blink was detected or be setting the residual wavefront error signal 222 to zero, depending on the control method.

In an alternative embodiment, the amount of time waited is a function of the amount by which the pupil size has decreased or the rate at which pupil size is decreasing. The blinking speed, and rate can be highly variable and dependent upon the testing conditions. Steps 338 and 340 combined together to determine when a blinking event occurs. In another alternative embodiment, other techniques are used to determine when a blinking event occurs. Examples of such techniques include but are not limited to motion detection and image analysis which can be used to determine if the eye is blinking this may be done by determining if an eyelid or an eyelash is interfering with the detection of the wavefront.

If in the fourth step 338 the controller 116 has determined that the eye 111 was not in the process of blinking when wavefront was measured then the controller 116 moves on to the eighth step 344. In the eighth step 344, the controller 116 adjusts the wavefront using the wavefront correction device 108 by first calculating a new control signal 224 u(t+1) in response to the residual wavefront error signal 222 measured at time (t). The new control signal 224 u(t+1) may be calculated using standard control methods for closed loop feedback control such as linear control, proportional control, PID control, fuzzy logic, and others. The new control signal 224 u(t+1) may be a function k( ) of the old control signal 224 u(t) and the residual wavefront error signal 222 e(t); u(t+1)=k(u(t+1), e(t)).

In one embodiment, the new control signal 224 u(t+1) includes information representing the size and position of the control area on which wavefront correction is performed. In another embodiment, the control signal 224 u(t+1) includes information representing, the size of the control area, the position of the control area, and the wavefront correction information. In another embodiment, the size and position of the control area are encoded into the values which represent the wavefront correction information over the entire range of the wavefront correction device. In particular, the control signal 224 may be an array of values each element in the array representing a set point for a specific position on the correction device 108. When a specific outside position on the correction device corresponds to a position outside of the pupil then the element of the array of control signal 224 that corresponds to the specific outside position may have a specific value that represents that state.

In one embodiment, when the eye is not blinking, a feedback control loop is used to control the state of the wavefront correction device based upon the most recent detected wavefront state. In another embodiment, the feedback control loop is used to control the state of the wavefront correction device based upon the most recent detected wavefront state and one or more previous detected wavefront states. In which case, when the controller determines that the blinking has stopped, the feedback control loop is reset and only the most recent detected wavefront state is used to control the state of the wavefront correction device. In another alternative embodiment, when the controller determines that the blinking has stopped, the feedback control loop is reset and only the most recent detected wavefront state and the detected wavefront state prior to the blinking being detected is used to control the state of the wavefront correction device.

This method allows you to stabilize the AO control against blinking. In the meantime, the non-blinking pupil change is taken care of, so AO can compensate for the aberration with various pupil sizes dynamically. Robustness and stableness of AO control can thus be improved.

Hartmann Images

Figure 4A:
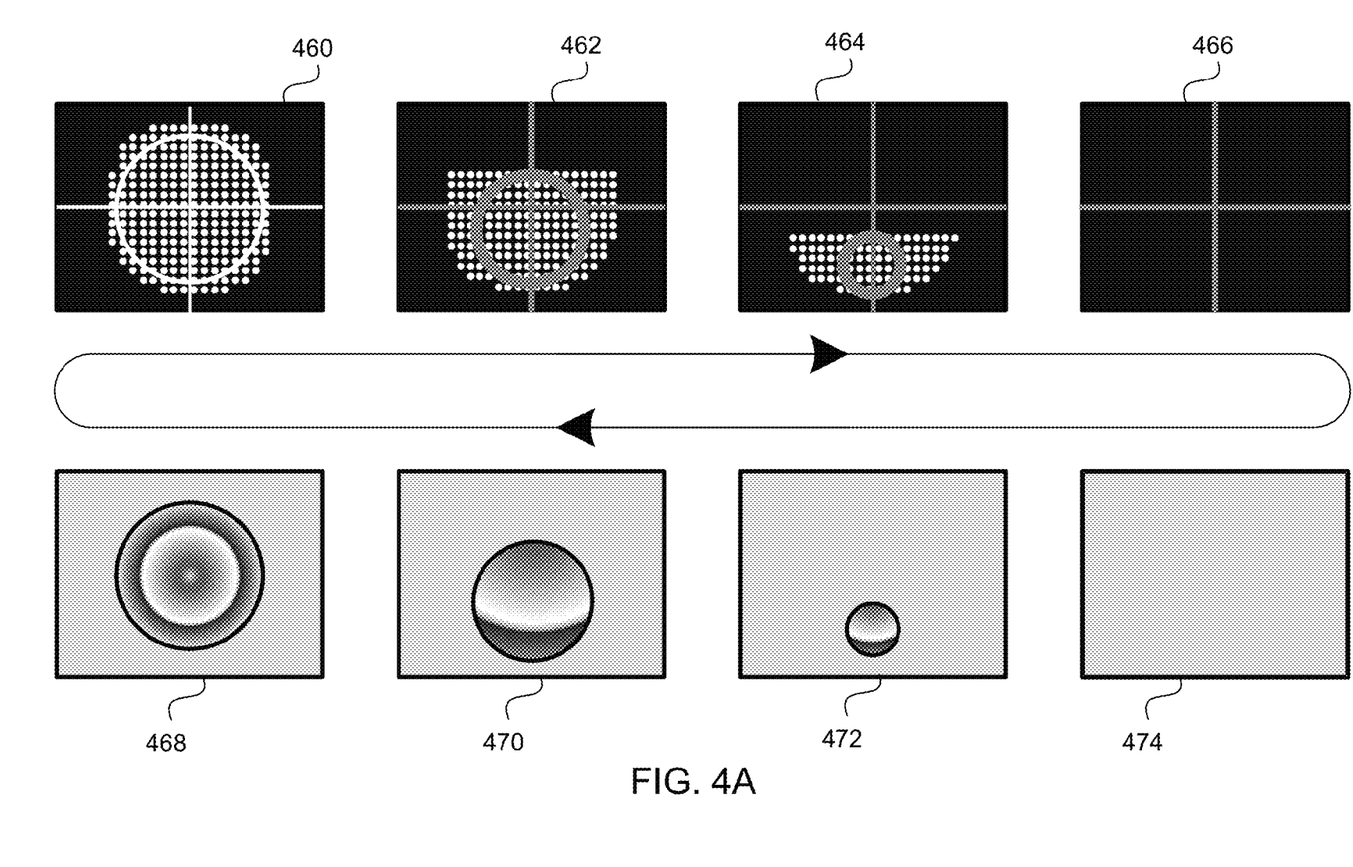
FIGS. 4A-B are illustrations of images used in an exemplary embodiment.

FIG. 4A is an illustration of 4 Hartmann images representing images that are taken before during and after the blink process. The first Hartman image 460 represents an exemplary image which could have been taken before or after the eye 111 was blinking. The white circle in the Hartmann image 460 represents a size and position of the pupil detected from a normal Hartmann image relative to the white cross hairs. The white dots in the Hartmann image represent an estimation of the wavefront error at each point. When the wavefront is perfectly flat collimated wavefront then each dot would be centered on a spot on a grid. The direction and distance of each spot from the ideal grid point is representative of the wavefront magnitude and direction of the wavefront error.

The second Hartman image 462 represents an exemplary image which could have been during the blinking process. The gray circle in the Hartmann image 462 represents a calculated size and position of the pupil detected from a normal Hartmann image relative to the gray cross hairs. Please note that this is not representative of the actual size and position of the pupil but size and position of a calculated pupil based on the second Hartmann image 462 which was taken during the blinking process. Note how the gray circle in the second Hartman image 462 is smaller than the first Hartman image 462, and how it is displaced below the crosshairs relative to the previous circle. This is an indication of blinking The third Hartmann image 464 also represents an exemplary image which could have been made during the blinking process. Note how the gray circle in the third Hartman image 464 is smaller than the second Hartman image 462, and how it is displaced below the crosshairs even more than the previous circle. The fourth Hartmann 466 represents an exemplary image which could have been made during the blinking process, while the eyelid interferes completely with pupil detection process. As the blinking continues and the eye reopens such that an image similar to the third Hartmann image 464, then an image similar to the second Hartmann image 462, then finally an image similar to the fourth Hartmann image is taken. In which case, the blinking process is finished and normal OA control can be resumed but in this case based upon the AO control signal from before the blinking was detected.

Images 468-474 are illustrations of the wavefront correction signal 224 that is sent to wavefront correction device 108 which may be a liquid crystal on silicon wavefront correcting device. Image 468 represents the wavefront correction signal based upon image 460. Images 470-472 represent the wavefront correction signals based upon image 462-464, notice how the wavefront correction signals represent pupils that are both shrunk and shifted down. Image 474 represents the wavefront correction signal based upon image 466, notice how no image is produced because no pupil is detected.

Figure 4B:
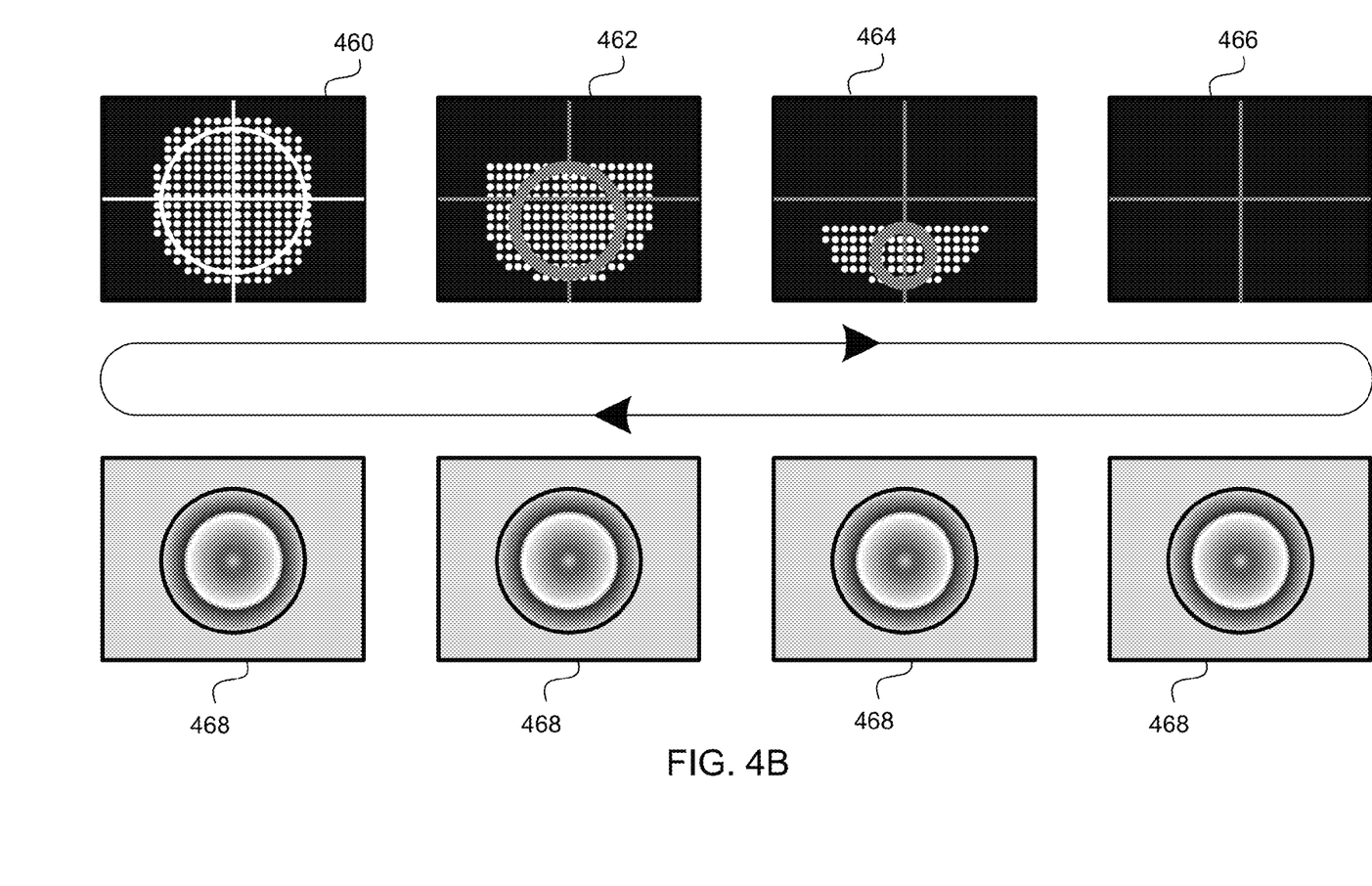

FIG. 4B is an illustration how image 468 replaces images 470-474 for the wavefront corrections signals sent to the wavefront corrections device. Instead of sending a signal based on the detected wavefront, the previous state of the wavefront correction device is maintained. This may be done by constantly sending the same wavefront correction signal when blinking is detected. Alternatively, this may be done by having a wavefront correction device 108 that maintains the same wavefront correction state until it is told to update the wavefront, in which case the controller 116 sends no information to wavefront correction device 108 while blinking is detected. In another alternative, the controller 116 may send a signal to the wavefront correction device 108 to maintain the current wavefront correction state.

Figure 5A:
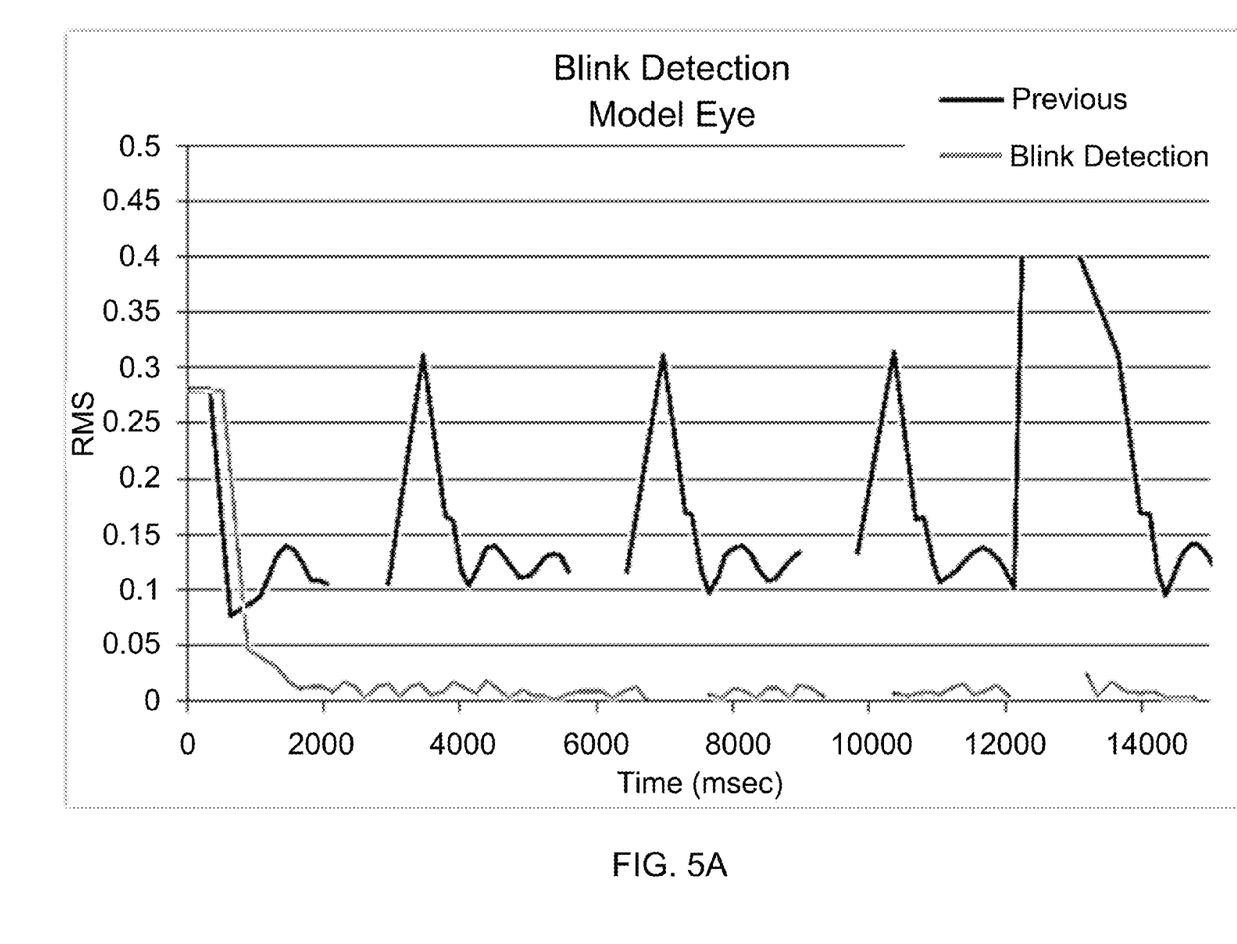
FIGS. 5A-B are illustrations of time series of the RMS error.
Figure 5B:
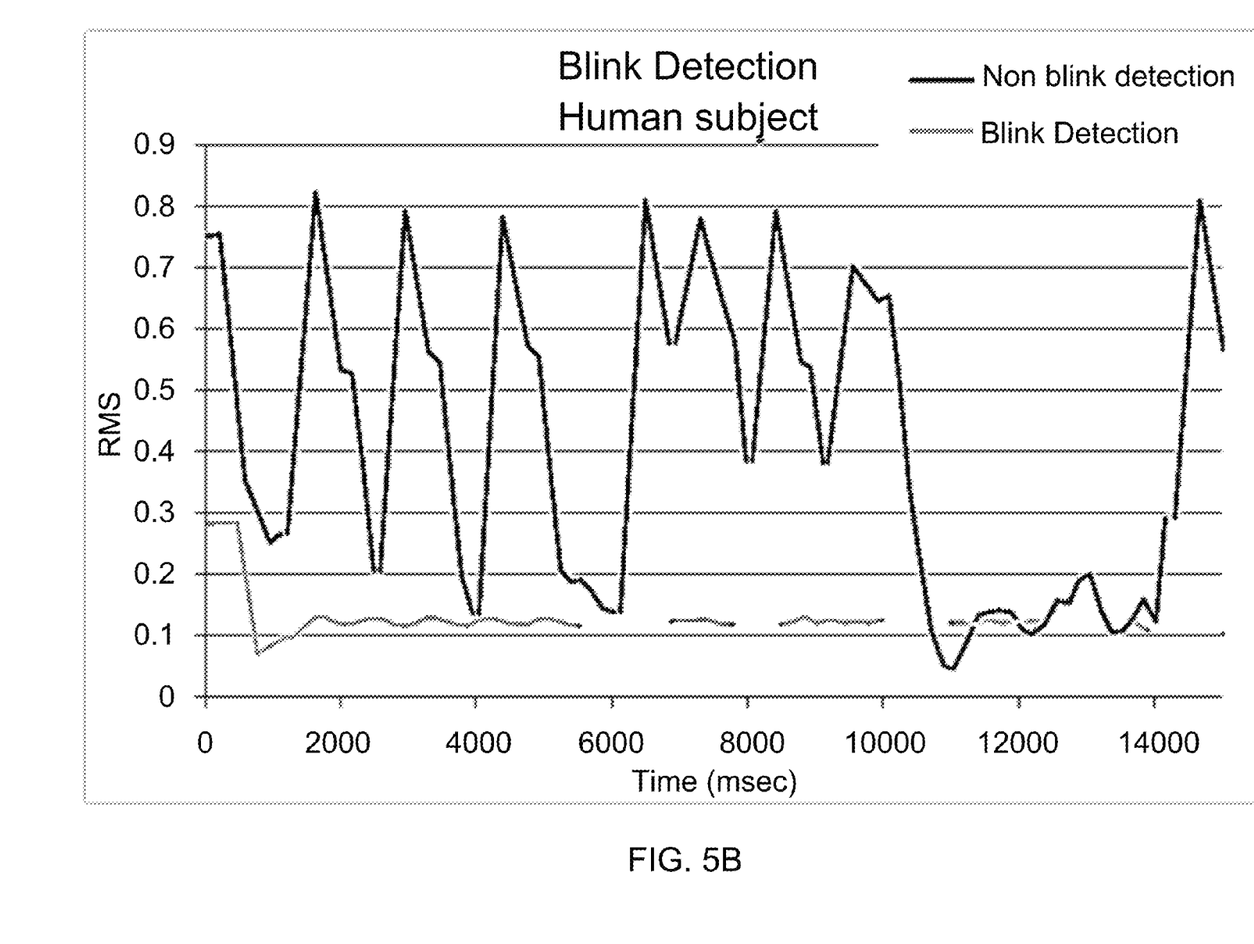

FIG. 5A is an illustration of a time series of the RMS (root mean square) error using a model eye. The dark line is the RMS error without blink detection. The gray line is RMS error with blink detection. FIG. 5B is an illustration of a time series of the RMS error using a human eye. The dark line is the RMS error without blink detection. The gray line is RMS error with blink detection.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An optical imaging system for imaging a subject eye comprising:
   one or more optical components configured to receive light from a light source, and configured to transmit the light received from the light source to a subject eye to be imaged;
   an aberration detection device that measures an aberration state of reflected light from the subject eye;
   a controller that determines a condition of the subject eye based on the aberration state of the reflected light measured by the aberration detection device, determines if the subject eye is in a second condition by detecting a size change of the reflected light on the aberration detection device, and determines if the subject eye is in a first condition if the controller determines that the subject eye is not in the second condition; and
   an aberration correction device that is configured to adjust an aberration state of reflected light transmitted to the subject eye, wherein:
      in a first case if the subject eye is in the first condition then the aberration correction device adjusts the light transmitted to the subject eye based on the aberration state of the reflected light measured by the aberration detection device in the first condition; and
      in a second case if the subject eye is in the second condition then the aberration correction device adjusts the aberration state of the light transmitted to the subject eye based on a most recent aberration state of the reflected light measured by the aberration detection device in the first condition prior to detecting that the subject eye is in the second condition,
   wherein the second condition is that the eye is in the process of blinking, and
   the first condition is that the eye is not in the process of blinking.

2. The optical imaging system according to claim 1, wherein determining that the subject eye is in the process of blinking is detected by:
   calculating a change in a size of a pupil of the subject eye based upon a size of the reflected light on the aberration detection device; and
   calculating a change in a position of the pupil of the subject eye based upon a specific position of the reflected light on the aberration detection device.

3. The optical imaging system according to claim 2, wherein:
   if the change in the size of the pupil indicates that pupil size has decreased relative to a previous size of the pupil when the subject eye was last determined to be in the first condition; and
   if the change in the position is such that a vertical displacement of the pupil is larger than a horizontal displacement of the pupil, relative to a previous position of the pupil when the subject eye was last determined to be in the first condition,
   then the subject eye is determined to be in the process of blinking,
   otherwise the subject eye is determined to not be in the process of blinking.

4. The optical imaging system according to claim 1, wherein the aberration correction device adjusts one or both of:
   aberration state of the reflected light from the subject eye, and
   aberration state of the light transmitted to the subject eye.

5. The optical imaging system according to claim 1, wherein the aberration correction device is a wavefront correction device.

6. The optical imaging system according to claim 5, wherein the wavefront correction device is selected from one or more of a tip-tilt mirror, a deformable mirror, a fluidic lens, and a spatial light phase modulator.

7. The optical imaging system according to claim 1, wherein the aberration detection device is a wavefront sensor.

8. The optical imaging system according to claim 7, wherein the wavefront sensor is a Shack-Hartmann sensor.

9. The optical imaging system according to claim 1, wherein if the controller detects eye lid or eye lash movement then the controller determines that the subject is in the second condition.

10. The optical imaging system according to claim 1, wherein in the second case the aberration correction device maintains the aberration state of the light transmitted to the subject eye while the subject eye is in the second condition until the subject eye returns to the first condition.

11. The optical imaging system according to claim 1, wherein when the subject eye switches from the second condition to the first condition, a process control loop that includes the aberration detection device and aberration correction device is reset.

12. The optical imaging system according to claim 1, further comprising the light source.

13. The optical imaging system according to claim 1, further comprising one or more scanners for scanning the light transmitted to the subject eye across the subject, and a detector for detecting the reflected light from the subject eye.

14. The optical imaging system according to claim 1, wherein determining if the subject eye is in the second condition is determined by:
   calculating a change in a size of the subject eye based upon a size of the reflected light on the aberration detection device.

15. The optical imaging system according to claim 1, wherein determining if the subject is in the second condition is determined by:
   calculating a change in a position of the subject based upon a specific position of the reflected light measured by the aberration detection device.

16. The optical imaging system according to claim 1, wherein the aberration detection device is a Shack-Hartmann sensor, and
   the controller detects spots in a Hartmann image of the Shack-Hartmann sensor, detects an area in the Hartmann image filled with spots, calculates a largest circle inside the detected area, and determines the condition of the subject eye based on the largest circle.

17. A method for controlling an imaging system for imaging a subject eye, the method comprising:

measuring an aberration state of reflected light from the subject eye with an aberration detection device;
detecting a condition of the subject eye based on a state of the light on the aberration detection device with a controller;
determining with the controller if the subject is in a second condition by detecting a size change of the reflected light on the aberration detection device, and determines if the subject eye is in a first condition if the subject eye is not in the second condition; and
adjusting an aberration state of light transmitted to the subject eye with an aberration correction device, wherein:
  in a first case if the subject eye is in the first condition then the aberration state of the light transmitted to the subject eye is adjusted based on the aberration state of the reflected light in the first condition; and
  in a second case if the subject eye is in the second condition then the state of the light transmitted to the subject eye is adjusted based on a most recent aberration state in the first condition prior to determining that the subject eye is in the second condition,
wherein the second condition is that the eye is in the process of blinking, and
the first condition is that the eye is not in the process of blinking.

18. A non-transitory computer readable medium encoded with instructions for controlling an imaging system for imaging a subject eye, which, when executed by a processor, perform the steps comprising:
measuring an aberration state of reflected light from the subject eye with an aberration detection device;
detecting a condition of the subject eye based on a state of the light on the aberration detection device with a controller;
determining with the controller if the subject is in a second condition by detecting a size change of the reflected light on the aberration detection device, and determines if the subject eye is in a first condition if the subject eye is not in the second condition; and
adjusting an aberration state of light transmitted to the subject eye with an aberration correction device, wherein:
  in a first case if the subject eye is in the first condition then the aberration state of the light transmitted to the subject eye is adjusted based on the aberration state of the reflected light in the first condition; and
  in a second case if the subject eye is in the second condition then the state of the light transmitted to the subject eye is adjusted based on a most recent aberration state in the first condition prior to determining that the subject eye is in the second condition,
wherein the second condition is that the eye is in the process of blinking, and
the first condition is that the eye is not in the process of blinking.

19. An optical imaging system for imaging a subject eye comprising:
an aberration measurement device that measures an aberration state of reflected light from the subject eye irradiated with measurement light;
an aberration adjustment device that adjusts at least one of the aberration states of the reflected light and the measurement light; and
a controller that detects a size change and a center position displacement of the reflected light on the aberration measurement device based on spots information detected by the aberration measurement device, and determines whether the subject eye is in a process of blinking or in a non-blinking based on the detected size change and the detected center position displacement of the reflected light on the aberration measurement device, wherein
in a first case where the subject eye is in the non-blinking, the aberration adjustment device adjusts the aberration state of the light transmitted to the subject eye based on the aberration state of the reflected light measured by the aberration detection device in the non-blinking, and
in a second case where the subject eye is in the process of blinking, the aberration adjustment device maintains a previous state of the aberration adjustment device based on the aberration state measured by the aberration measurement device before the process of blinking is detected.

20. The optical imaging system according to claim 19, wherein the controller determines whether a vertical displacement of the center position displacement is larger than a horizontal displacement of the center position displacement, and determines that the subject eye is in a process of blinking when the size change decreases and the vertical displacement of the center position displacement is larger than the horizontal displacement of the center position displacement.

21. The optical imaging system according to claim 19, wherein if the subject eye is not in the process of blinking, the aberration adjustment device adjusts the measurement light based on the aberration state of the reflected light measured by the aberration measurement device, and
wherein if the subject eye is in the process of blinking, the aberration adjustment device adjusts the measurement light based on a most recent aberration state of the reflected light measured by the aberration measurement device.

22. The optical imaging system according to claim 19, wherein the aberration measurement device includes Shack-Hartmann sensor,
wherein output data of the aberration measurement device is a Hartmann image.

23. The optical imaging system according to claim 22, wherein the controller detects the size change using the largest circle inside the Hartmann image on the Shack-Hartmann sensor.

24. The optical imaging system according to claim 23, wherein the controller detects the size change based on a diameter of the circle.

25. The optical imaging system according to claim 19, further comprising a device that generates an image of the subject eye based on the reflected light adjusted by the aberration adjustment device.

26. A method for controlling an optical imaging system for imaging a subject eye, the method comprising:
measuring, with an aberration measurement device, an aberration state of reflected light from the subject eye irradiated with measurement light;
detecting a size change and a center position displacement of the reflected light on the aberration measurement device based on spots information detected by the aberration measurement device, and determining whether the subject eye is in a process of blinking or in a non-blinking based on the detected size change and the detected center position displacement of the reflected light on the aberration measurement device; and adjusting at least one of the aberration states of the reflected light and the measurement light with an aberration adjustment device based on whether the subject eye is in the process of blinking, wherein in a first case where the subject eye is in the non-blinking, the aberration state of the light transmitted to the subject eye is adjusted by the aberration adjustment device based on the aberration state of the reflected light measured by the aberration detection device in the non-blinking, and in a second case where the subject eye is in the process of blinking, a previous state of the aberration adjustment device is maintained by the aberration adjustment device based on the aberration state measured by the aberration measurement device before the process of blinking is detected.

* * * * *